(12) United States Patent
Hesseldahl (10) Patent No.: US 8,011,506 B2
(45) Date of Patent: Sep. 6, 2011

(54) TRAY FOR HANDLING SYRINGES

(75) Inventor: Flemming Hesseldahl, Slagelse (DK)

(73) Assignee: Moller & Devicon A/S, Sandved (DK)

( * ) Notice: Subject to any disclaimer, the term of this patent is extended or adjusted under 35 U.S.C. 154(b) by 324 days.

(21) Appl. No.: 11/721,327

(22) PCT Filed: Dec. 8, 2005

(86) PCT No.: PCT/DK2005/000777
§ 371 (c)(1),
(2), (4) Date: Jun. 24, 2009

(87) PCT Pub. No.: WO2006/061022
PCT Pub. Date: Jun. 15, 2006

(65) Prior Publication Data
US 2009/0288973 A1 Nov. 26, 2009

(30) Foreign Application Priority Data
Dec. 8, 2004 (EP) ..................... 04388088

(51) Int. Cl.
*B65D 83/10* (2006.01)
*A47F 7/00* (2006.01)

(52) U.S. Cl. ..................... 206/366; 211/85.13

(58) Field of Classification Search .......... 206/365–366, 206/443, 557–565; 211/60.1, 85.13
See application file for complete search history.

(56) References Cited

U.S. PATENT DOCUMENTS

| | | | |
|---|---|---|---|
| 2,084,540 A * | 6/1937 | Smith | 206/365 |
| 2,887,215 A * | 5/1959 | Hutchison | 206/365 |
| 3,133,635 A * | 5/1964 | Gordon et al. | 206/366 |
| 3,267,636 A | 8/1966 | Sternberg | |
| 3,305,084 A * | 2/1967 | Higgins et al. | 206/366 |
| 4,500,247 A | 2/1985 | McKnight et al. | |
| 4,863,451 A | 9/1989 | Marder | |
| 5,934,859 A | 8/1999 | Goetzelmann | |
| 6,216,885 B1 | 4/2001 | Guillaume | |
| 7,048,120 B2 * | 5/2006 | Pond | 206/366 |

FOREIGN PATENT DOCUMENTS

| | | |
|---|---|---|
| DE | 3638448 | 5/1988 |
| EP | 0790063 | 8/1997 |
| WO | WO 00/64749 | 11/2000 |

OTHER PUBLICATIONS

Written Opinion on corresponding PCT application (PCT/DK2005/000777) from International Searching Authority (EPO) dated Feb. 10, 2006.

* cited by examiner

*Primary Examiner* — Bryon P Gehman
(74) *Attorney, Agent, or Firm* — Klein, O'Neill & Singh, LLP (57) ABSTRACT

A tray is provided for receiving a plurality of pre-filled syringes each having a tubular body defining an outer surface and a chamber having an open first end sealed with a plug and an open opposite second end configured to establish fluid communication with a hypodermic needle, wherein a flange extends from the tubular body at the first end. The tray includes a plate defining a plurality of through-going ridges and a plurality of through-going grooves parallel to the ridges, wherein the ridges are interconnected with the grooves. A multitude of open apertures is defined at the ridges, wherein the apertures are configured for (a) receiving the flange of a syringe received between two adjacent ridges, and (b) permitting the passage of a gas through the plate to contact the outer surface of the syringe.

16 Claims, 4 Drawing Sheets

TRAY FOR HANDLING SYRINGES

CROSS-REFERENCE TO RELATED APPLICATION

This application is a national phase filing, under 35 U.S.C. §371(c), of International Application No. PCT/DK2005/000777, filed 8 Dec. 2005, the disclosure of which is incorporated herein by reference in its entirety.

FEDERALLY SPONSORED RESEARCH OR DEVELOPMENT

Not Applicable

BACKGROUND OF THE INVENTION

The present invention relates to a method for handling syringes, a tray for receiving syringes and a system for handling syringes.

Within the technique, numerous examples describe various techniques and various trays or similar structures for the handling of syringes. Examples of handling of syringes involve the transfer from a filling station to an autoclave station or to a further on to a packaging station. During the handling, the syringes must be kept safe without being exposed to mechanical impact causing the syringes to be destroyed and also allowing easy access to the syringes for e.g., the autoclaving process or for the transfer of the syringes to or from a tray in e.g., a packaging station.

Examples of techniques of this kind are presented in U.S. Pat. No. 6,685,017, WO 03/06209, US 2003 0132129, EP 1 061 975, WO 99/45985, U.S. Pat. No. 6,250,052, US 2004 0017981, U.S. Pat. No. 5,360,410, WO 93/02720, U.S. Pat. No. 6,792,743, EP 1 433 705, US2002 0069616, U.S. Pat. No. 6,263,641, U.S. Pat. No. 6,189,292, U.S. Pat. No. 6,164,044, WO 99/45984, U.S. Pat. No. 5,934,859, U.S. Pat. No. 4,438,845, U.S. Pat. No. 5,007,535, U.S. Pat. No. 4,753,345, WO 91/15411, DE 36 38 448, EP 0 790 063, U.S. Pat. No. 3,267,636 and WO 00/64749.

The reference U.S. Pat. No. 5,934,859 discloses a device for handling syringes. A moulded tray made of plastic and having ribs is further disclosed. Syringes are held in the tray by means of tray nubs formed in the ribs.

The reference U.S. Pat. No. 4,500,247 discloses a system for inspecting filled hypodermic syringes.

The reference U.S. Pat. No. 6,216,885 discloses a tray for grouping together syringes. The tray is described as being produced from a sheet of thermo-formed plastic material. Syringes are described as being held in place by two protuberances, which elastically deflect in one direction for insertion of a syringe and in the other direction when the syringe is removed from the tray.

Reference is made to the above mentioned patent applications and patents, and the above US patents and patent applications are hereby incorporated in the present specification by reference.

SUMMARY OF THE INVENTION

An object of the present invention is to provide a novel technique including a method, a tray and a plant for the safe, swift and easy handling of syringes, in particular syringes of different sizes in a compact and easy to handle tray allowing the syringes to be shifted to and from various stations including the above-mentioned stations. A feature of the present invention relates to the fact that the novel technique of handling a multiplicity of syringes by means of a tray allows the autoclaving of the syringes when supported in the tray characteristic of the present invention.

A particular feature of the present invention relates to the fact that the handling of the syringes by means of the tray characteristic of the present invention allows a large number of syringes to be handled by means of a forklift truck since the tray is adapted to the standard Euro-pallet system. In some embodiments the tray may have a geometry substantially corresponding to half the size of a Euro-pallet, i.e. two trays may be positioned on a Euro-pallet without any parts hanging outside of the Euro-pallet.

The above object, the above feature and the above advantage together with numerous other objects, features and advantages which should be evident from the below detailed description of presently preferred embodiments of the present invention relate according to a first aspect of the present invention to a method of handling a first plurality of pre-filled syringes each comprising a tubular body defining a first and an opposite second end, the first and the second end being open ends, the tubular body defining a chamber wherein a substance is stored, the first end sealed with a plug, the second end adapted to establish fluid communication to a hypodermic needle, at least one flange extending from the tubular body, the first plurality of syringes being held in the at least one extending flange so that each of the syringes are in a substantially vertical orientation, the method comprising:

providing an assembly defining an inlet and an outlet,
the first plurality of syringes provided at the inlet,
providing a tray comprising a second plurality of recesses for receiving the first plurality of syringes, the recesses defined by through going parallel ridges and grooves, a multitude of apertures being defined at the ridges for receiving the at least one flange of a specific syringe received between two adjacent ridges,
transferring the first plurality of syringes from the inlet into the tray in a substantially horizontal orientation, and
the tray transferred into a frame positioned at or near the outlet.

The second end of the syringes may also be sealed for ensuring that no contamination reaches the substance inside the syringe. The syringes are preferably of a sort widely, and readily, commercially available, and may have any size or shape and crafted in any material.

In a presently preferred embodiment of the present invention, the substance is a medical substance, a medicament, a medicine, a drug or the like.

The assembly may be constituted by a machine, apparatus or the like, for handing the mentioned plurality of syringes.

The tray is preferably adapted to receiving more than one syringe at a time, and may be adapted to receive more than the plurality of syringes provided, especially if that plurality is a low number, in which case the tray may receive multiple pluralities of syringes, e.g. by filling the tray several times.

The syringes may be received from, or alternatively a tray filled or partly filled being passed on to, an inspection station, where the pre-filled syringes are inspected to establish if any contamination is present in the syringe and/or the substance inside the syringe.

Also, the syringes may be received from, or alternatively a tray filled or partly filled being passed on to, a marking station e.g. marking the individual syringes with a label, printing on the syringe body or the like with an indication of the contents of the syringe.

The transfer of the syringes may by obtained in several ways, especially by:

providing a first wheel mounted in the frame at the inlet, the first wheel defining a first periphery and a first multitude of indentations defined at the first periphery, each of the first multitude of indentations including holding devices for holding a syringe, the plurality of syringes provided to the first wheel at the first multitude of indentations, the first wheel defining a first plane, the wheel mounted so that the first plane is in a horizontal orientation, providing a second wheel mounted in the frame at the inlet, the second wheel defining a second periphery and a second multitude of indentations defined at the second periphery, each of the second multitude of indentations including holding devices for holding a syringe, the plurality of syringes provided to the second wheel at the second multitude of indentations, the second wheel defining a second plane, the wheel mounted so that the second plane is in a horizontal orientation, a specific angle defined between a first and a second normal to the first and the second plane respectively, and transferring the plurality of syringes from the first wheel to the second wheel and transferring the plurality of syringes from the second wheel to the tray.

The two wheels receive the syringes at the inlet, or from a transfer device mounted at or near the inlet. The angle defined between the two wheels is contemplated to enable the transfer of the syringes from an orientation being substantially vertical into an orientation being substantially horizontal. The angle may be defined or measured between any of the components defining the planes. Mathematically, the plane may be defined by three vectors and/or a vector being normal to the plane.

One way of defining the angle is between a first component of a normal to the first plane and a second component of the normal to the second plant. Specifically, the specific angle may be defined between a first component of the first normal and a second component of the second normal in the interval 0 to 180 degrees, such as 15 to 160 degrees, such as 40 to 100 degrees, such as 40 to 85 degrees, such as 42 to 70 degrees, such as 44 to 50 degrees, such as 0 to 20 degrees, such as 20 to 40, degrees, such as 40 to 50 degrees, such as 50 to 75 degrees, such as 75 to 85 degrees, such as 85 to 100 degrees, such as 100 to 180, preferably 45 degrees.

An alternative embodiment, the transferring of the syringes from the inlet to the tray is obtained by:

providing a robotic arm comprising a gripping part for gripping at least one syringe at a time, and the robotic arm transferring the plurality of syringes from the inlet to the tray at least one at a time.

The robotic arm transfers a specific number of syringes at one time into the tray, the operation may be repeated until the entire plurality of syringes is transferred. The robotic arm may comprise several joints for transferring the syringes from a substantially vertical orientation into the substantial horizontal orientation.

The frame may comprise a base defining an upper base surface and at least one supporting beam extending from the upper base surface. The base may be used for storing trays being empty, filled or half-filled with syringes. The base may advantageously define an overall geometry corresponding to a Euro-pallet. The Euro-pallet geometry enables the base to be handled by machinery widely available, such as forklift trucks and the like.

A feature of the frame relates to the frame being made from a corrosion-resistive material, preferably being a metallic material, capable of withstanding fumigation, disinfection, hot steam, water, sterilisation by autoclave or any combinations thereof.

Alternatively, the frame may be a hollow frame of any material, preferably having one or more of the attributes mentioned above. Further alternatively, the frame may have a core material such as wood or other material not having any of the above mentioned attributes, and a coating having one or more of the above mentioned attributes.

The above object, the above feature and the above advantage together with numerous other objects, features and advantages which should be evident from the below detailed description of presently preferred embodiments of the present invention relate according to a second aspect of the present invention to a tray for receiving a first plurality of pre-filled syringes each comprising a tubular body defining a first and an opposite second end, the first and the second end being open ends, the tubular body defining a chamber wherein a substance is stored, the first end sealed with a plug, the second end adapted to establish fluid communication to a hypodermic needle, at least one flange extending from the tubular body at the first end, the tray comprising:

a plate defining a second plurality of through going ridges and a third plurality of through going grooves parallel to the ridges, the ridges interconnected with the grooves, and a multitude of apertures defined at the ridges for receiving the at least one flange of a specific syringe received between two adjacent ridges.

The plate is preferably made from a corrosion-resistive material, preferably being a metallic material, capable of withstanding fumigation, disinfection, hot steam, water, sterilisation by autoclave or any combinations thereof. The plate may e.g. be made from stainless steel, aluminium, a combination or composition of metallic materials, or a rigid and/or hard plastic material.

The tray is preferably made from a single piece of material; however, the plate may alternatively be made from two or more pieces of material, preferably being of the same type of material, but not necessarily.

A special advantage of the present invention relates to a tray according to the present invention, wherein the multitude of apertures are distributed in a spacing slightly exceeding the length defined between the first and the second end of the syringe.

The distance between two apertures preferably exceeds the length defined between the ends of the syringe being handled, i.e. the overall length of the syringe.

Positioning the apertures closer results in the syringes not being placed in an optimal package ratio in the tray, a placement at a greater distance also resulting in an area of unused space, however, it is preferable to ensure that a, small, spacing exists between a second end of one syringe and a first or second end of a syringe positioned nearby.

A specific feature of the present invention relates to the tray, wherein the multitude of apertures may define a geometry being square, circular, elliptical, triangular, polygonal or any combination thereof.

The apertures may define a geometry, where the geometry chosen may ensure that the at least one extending flange of the syringe may be received in that aperture.

The first plurality of ridges and/or the second plurality of grooves may be substantially parallel. Also, the tray may define a rectangular outer geometry, the tray further defining a short side and a long side, the tray further comprising two end-pieces placed at opposite ends of the tray, then the first plurality of ridges and/or the second plurality of grooves extend parallel to the long side or the short side.

In one embodiment of the tray according to the present invention, each of the end pieces may define a first breadth and a second breadth different from the first breadth. The first and second breath is defined at two locations on the end piece. The breaths are preferably measured at parallel locations. Preferably the breaths are defined at several locations, resulting in a jagged or serrated profile. This profile is contemplated to enable trays to be stacked in an improved manner so that the trays do not shift position during transport or due to uneven loads.

A special feature of the present invention relates to a first group of apertures that may define a first geometry and at least one additional group that may define at least one additional geometry different from or similar to the first geometry. The differences in geometry may be the first geometry being substantially square and another being substantially rectangular.

The difference in geometry may also be construed as differences in sizes, specifically, the first geometry may be a substantially rectangular geometry defining a first and a second width, the at least one additional geometry may be a substantially rectangular geometry defining a third and a fourth width, the first width being smaller than the third and/or the fourth width and the second width being smaller than the fourth and/or the third width, respectively. Alternatively, the first and the second widths may be equal and/or the third and the fourth widths may be equal.

A specific feature relates to the first group of apertures being distributed in-between the at least one additional group of apertures. The distribution of apertures along the length of the tray is contemplated to ensure that the same tray may be used with a variety of syringes each having a specific geometry and/or size.

In an advantageous embodiment of the present invention, the tray may be made of a rigid material. The rigid material may e.g. be steel, stainless steel, a hard plastic material, a combination or composition of more rigid materials, or any other rigid material.

It is an advantage that the ridges and the grooves may define a V-shaped geometry wherein the syringes may be received. The V-shaped geometry may then be defined in a cross-section of the tray, preferably as a number of grooves or tracks each having a V-shaped cross-section distributed across the width of the tray.

The V-shaped geometry may be formed such that a syringe received therein is supported by walls interconnecting a groove and adjacent ridges. The walls may be planar and define an angle between them. Depending on the height of the walls, the size of the syringe and the angle between the walls interconnecting a groove and adjacent ridges the syringe body may abut the walls or the groove.

The above object, the above feature and the above advantage together with numerous other objects, features and advantages which should be evident from the below detailed description of presently preferred embodiments of the present invention relate according to a third aspect of the present invention to a plant for handling a plurality of syringes each comprising a tubular body defining a first and an opposite second end, the first and the second end being open ends, the tubular body defining a chamber wherein a substance may be stored, the first end sealed with a plug, the second end adapted to establish fluid communication to a hypodermic needle, at least one flange extending from the tubular body, the plant comprising:

at least one filling station for filling the plurality of syringes, the first plurality of syringes being held in the at least one extending flange so that each of the syringes are in a substantially vertical orientation, an assembly defining an inlet, the assembly receiving the plurality of filled syringes from the at least one filling station in a substantially vertical orientation at the inlet, and the assembly further comprising a device for transferring the plurality of filled syringes from the substantially vertical orientation into a multitude of trays in a substantially horizontal orientation.

The filling station may also place plugs for sealing the first and/or the second ends of the syringes. The filling station preferably fills the syringes with a medical substance, as discussed in relation with the first aspect of the present invention.

The syringes, after being placed in a tray, may be passed on for further processing, such as to an autoclave, a packing station or the like.

Furthermore, the device may be constituted by:
a first wheel mounted in the frame at the inlet, the first wheel defining a first periphery and a first multitude of indentations defined at the first periphery, each of the first multitude of indentations including holding devices for holding a syringe, the plurality of syringes provided to the first wheel at the first multitude of indentations, the first wheel defining a first plane, the wheel mounted so that the first plane is in a horizontal orientation, a second wheel mounted in the frame at the inlet, the second wheel defining a second periphery and a second multitude of indentations defined at the second periphery, each of the second multitude of indentations including holding devices for holding a syringe, the plurality of syringes provided to the second wheel at the second multitude of indentations, the second wheel defining a second plane, the wheel mounted so that the second plane is in a horizontal orientation, a specific angle defined between a first and a second normal to the first and the second plane respectively, and the plurality of syringes transferred from the first wheel to the second wheel and the plurality of syringes transferred from the second wheel to the tray.

Alternatively, the device may be constituted by a robotic arm adapted for handling at least one syringe at a time.

The plant according to the third aspect of the present invention may incorporate any of the features of the method according to the first aspect of the present invention, and/or a tray as described in relation to the second aspect of the present invention.

BRIEF DESCRIPTION OF THE DRAWINGS

The present invention is now to be discussed in detail with reference to the figures, in which.

The figures are intended to illustrate a non-limiting embodiment of the present invention.

DETAILED DESCRIPTION OF THE INVENTION

Figure 1:
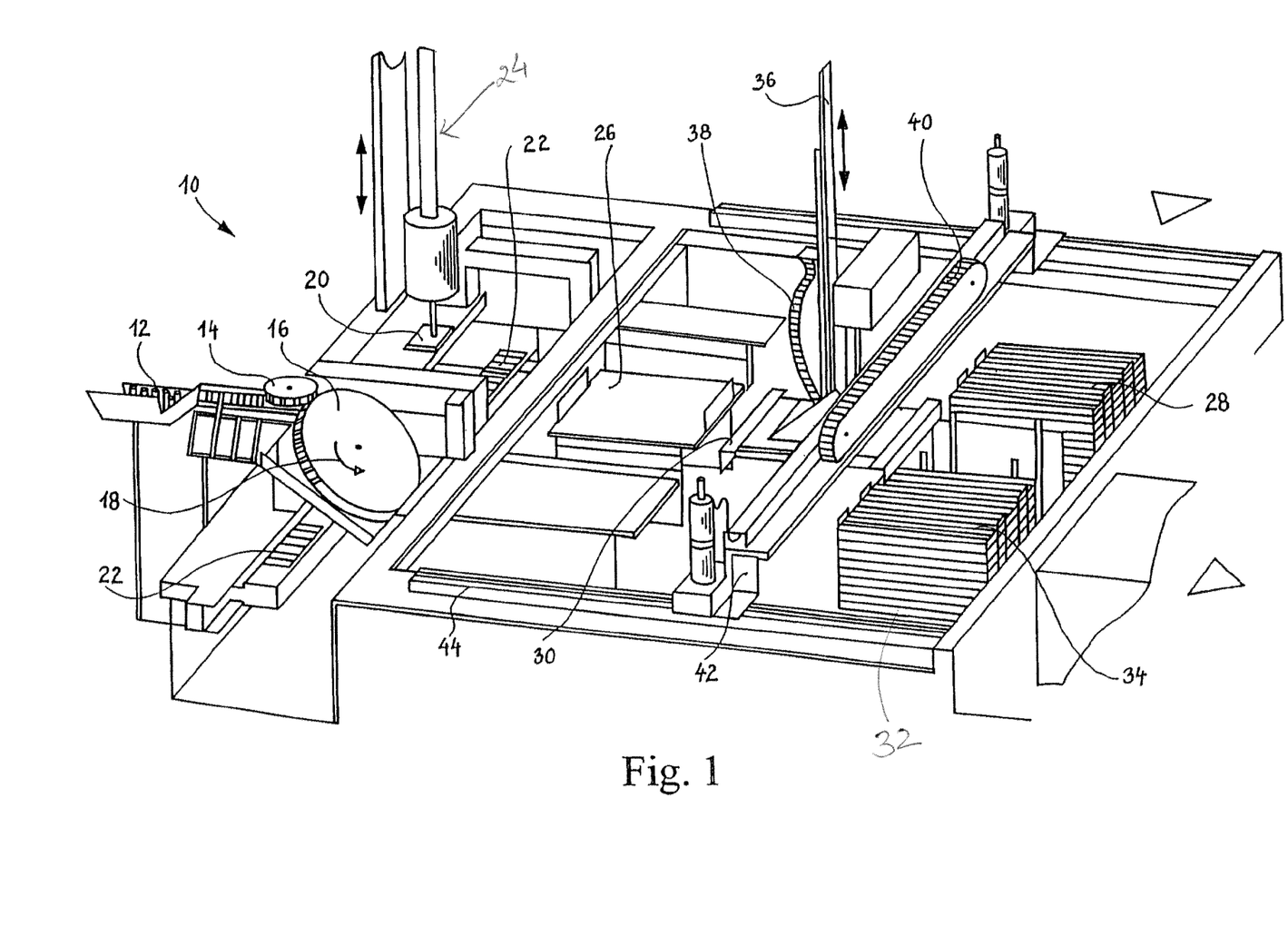
FIG. 1 is a schematic illustration of an apparatus according to the present invention.

FIG. 1 schematically illustrates a machine generally designated the reference numeral 10. A plurality of syringes is fed to an inlet, in the presently preferred embodiment of the present invention constituted by adjustable guidelines. In the presently preferred embodiment of the present invention, the syringes are received from a SAG filling line. From the guidelines, the syringes are passed on to two star wheels 14 and 16, and on into a handling subsystem of the machine 10.

The guidelines are fitted with two rubber belts driven by an AC-Electro-motor, capable of running with adjustable speed. The guideline brings the syringes to a lower level from the inlet, the rubber belts are contemplated to ensure that the speed of the syringes does not increase during the lowering. Optionally, queue sensors may be integrated in the guideline for detecting the fill level of the guideline. Sensors may detect low, normal and high levels.

The wheel 14 is positioned substantially horizontally and the wheel 16 is positioned at an angle substantially 45 degrees in relation thereto. The wheel 16 is a conical star wheel. The wheels 14 and 16 are fitted with suction cups, other fastening and/or gripping devices may be used.

The wheel 14 grips a syringe and transfers it from a substantially vertical position into a tray 20 in a substantially horizontal position via the wheel 16. The tray 20 is moved horizontally while one syringe at the time is placed in the tray 20. When the tray 20 is filled, the tray is moved to a position where all of the syringes in the tray 20 are emptied into a second tray 22. A tray corresponding to the tray 22 is illustrated in greater detail in FIGS. 3 and 4.

The tray 20 and the wheel 16 are rotated and moved, respectively, in synchronism. For improving the throughput of the machine, two trays corresponding to the tray 20 are used in the presently preferred embodiment of the present invention, of which only one is visible in FIG. 1. Using two trays enables one to be filled while the other is emptied. More trays may also be used.

The star wheel 14 and the conical wheel 16 are driven by one, alternatively two independent, servomotors. In case two independent servomotors are used, they are preferably driven in synchronism.

In a preferred embodiment, sensors for detecting the presence or non-presence of syringes in a specific location of one of the wheels 14 and 16 are included. The wheels preferably operate using suction cups or vacuum for holding the syringes.

The handling of the syringes is performed with a reciprocating grabber 24. The grabber 24 moves in at least one dimension, up and down, for grabbing the syringes out of the tray 20 and placing them into the tray 22. The tray 20 is then returned to be refilled. The grabber also moves sideways for ensuring that the syringes are positioned correctly in the tray 22, alternatively the tray 22 be moved to ensure that the syringes are placed correctly.

The grabber 24 and tray 20 constitute an intermediate transport system. In the presently preferred embodiment of the tray 20 up to 11 syringes may be placed in the tray 20. The distance between the individual syringes in the tray 20 is preferably equal to the distance between syringes placed in the tray 22.

After repeatedly emptying the tray 20 into the tray 22, the tray 22 becomes filled. The filled tray 22 is then moved using a tray handling system 26. The tray handling system 26 receives empty trays from a stack 28 of empty trays. The empty trays are brought from the stack 28 to the tray handling system 26 by a grabber 30.

When the tray 22 has been filled, the grabber 30 grabs the tray 22 and places it on a stack 32 for filled trays. The filled trays are stacked in a frame 34. In a presently preferred embodiment, the frame 34 has outer dimensions corresponding to a Euro-pallet. The frame 34 is preferably made from a metallic material, such as stainless steel.

When the frame 34 has been filled, the frame 34 may be picked up by a forklift-truck, alternatively by another machinery for handling pallets. The frame 34 with the trays filled with syringes may then be transported to further processing, such as disinfecting, fumigation, sterilisation, packaging, storage, further transportation or any combinations thereof.

The grabber 30 is mounted to a frame part 36, whereon a belt drive 38 for raising and lowering the grabber 30 is mounted. A belt drive 40 enables horizontal movement of the grabber 30. The frame part 36 and the belt drive 40 are mounted on a bar or frame part 42, which further is mounted on an outer frame 44.

The belt drives 38 and 40 are driven by two independent linear motors, each having positive and negative limit switches and a zero-point sensor.

Access to the racks 28 and 32 with empty trays and filled trays respectively, are obtained through a two-door system, ensuring that access to the machine during operation is not allowed. The doors are made from a poly-carbonate material and the surrounding frame is made from alu-profiles. Security devices are connected to the doors for controlling access through the doors. When the machine is in operational mode, access to the inner part of the machine is prohibited for ensuring that no harm is done to the operators or other people accessing the machine.

The doors are arranged in an outer door and an inner door. The inner door may not be opened if the outer door is open, and vice versa. The inner door may not be opened if the machine is in operation.

When the racks 28 and 32 are positioned prior to operating the machine, the racks 28 and 32 are held in place by holding devices, preferably constituted by pneumatic devices.

Initially, the rack 28 is filled with empty trays and the rack 32 is empty. After the trays have been filled, the rack 28 is empty and the rack 32 is filled with trays and the trays are filled with syringes to the desired amount.

Figure 2:
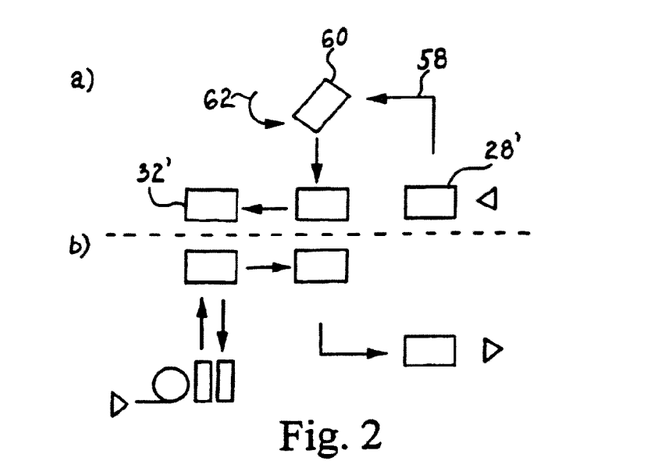
FIG. 2 is a schematic illustration of the process of handling trays.

FIG. 2 schematically illustrates the path of travel of a tray from the initial position in the rack 28 to the final position in the rack 32. The tray is taken from the rack 28 illustrated by the position 28'. The tray is relocated, as indicated by the arrow 58, to a position 60 where the tray is filled with syringes. In the position 60, the tray may be rotated, as indicated by the arrow 62. After filling, or alternatively partly filling, the tray, the tray is moved to a storage position 32'.

Figure 3:
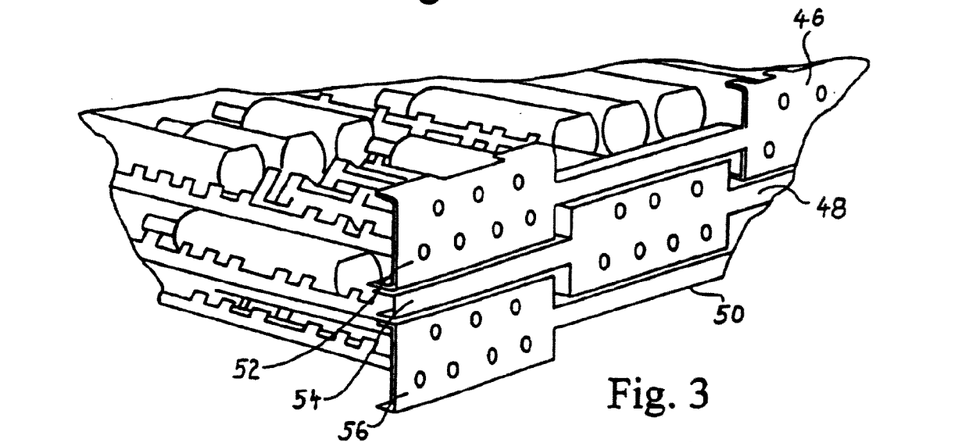
FIG. 3 is a schematic illustration of a stack with three trays.

FIG. 3 is a schematic illustration of a stack of three trays 46, 48 and 50. The trays 46, 48 and 50 comprise end pieces 52, 54, 56 that enables the trays to be stacked in a compact manner. The end pieces 52, 54 and 56 also ensures that the trays 46, 48 and 50 do not slide sideways in relation to each other.

Figure 4:
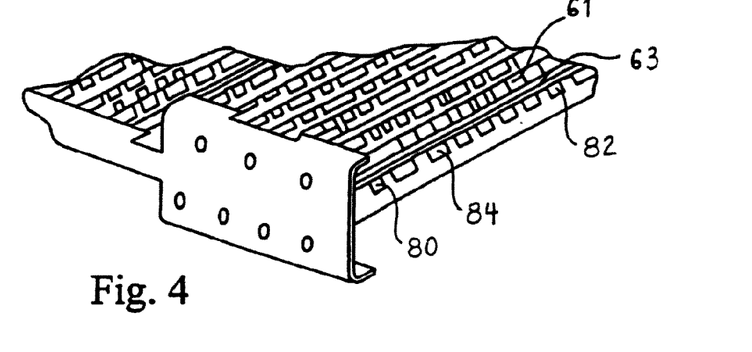
FIG. 4 is a schematic illustration of a tray according to the present invention.

FIG. 4 is a schematic illustration of a tray according to a presently preferred embodiment of the present invention. The body of the tray defines a corrugated surface. The corrugations define a number of recesses or grooves wherein the syringes are received. Furthermore, a number of apertures are defined in the body of the tray for receiving the extending flange of the syringes.

The tray defines a number of ridges 61 and a number of grooves 63. In the presently preferred embodiment of the present invention, the tray defines 20 grooves, allowing a maximum of 20 syringes in one row at one time. Some apertures are defined in the tray for receiving the flange of a syringe so that the syringe may be received in the groove. The size of the syringe and/or the flange varies from one size/type of syringe to another, therefore, the tray preferably includes at least two different sizes of apertures for enabling the same tray to be used with different types/sizes of syringes.

The apertures are preferably distributed according to a specific pattern, enabling a multitude of different syringes to be placed, positioned or received in the grooves of the tray.

In a presently preferred embodiment of the tray according to the present invention, the distance between two ridges is approximately 25 mm, and approximately 25 mm between two groove bottoms. The overall length of the tray is 762 mm and the width is 560 mm. The height of the end pieces is 47 mm.

In the presently preferred embodiment of the present invention, the tray includes apertures of two different sizes, small apertures with a size of 4×10 mm and larger apertures with a size of 6×36 mm.

The rack, in which the trays are placed, is divided into two areas having an inner geometrical configuration of 568×768 mm each.

Figure 5:
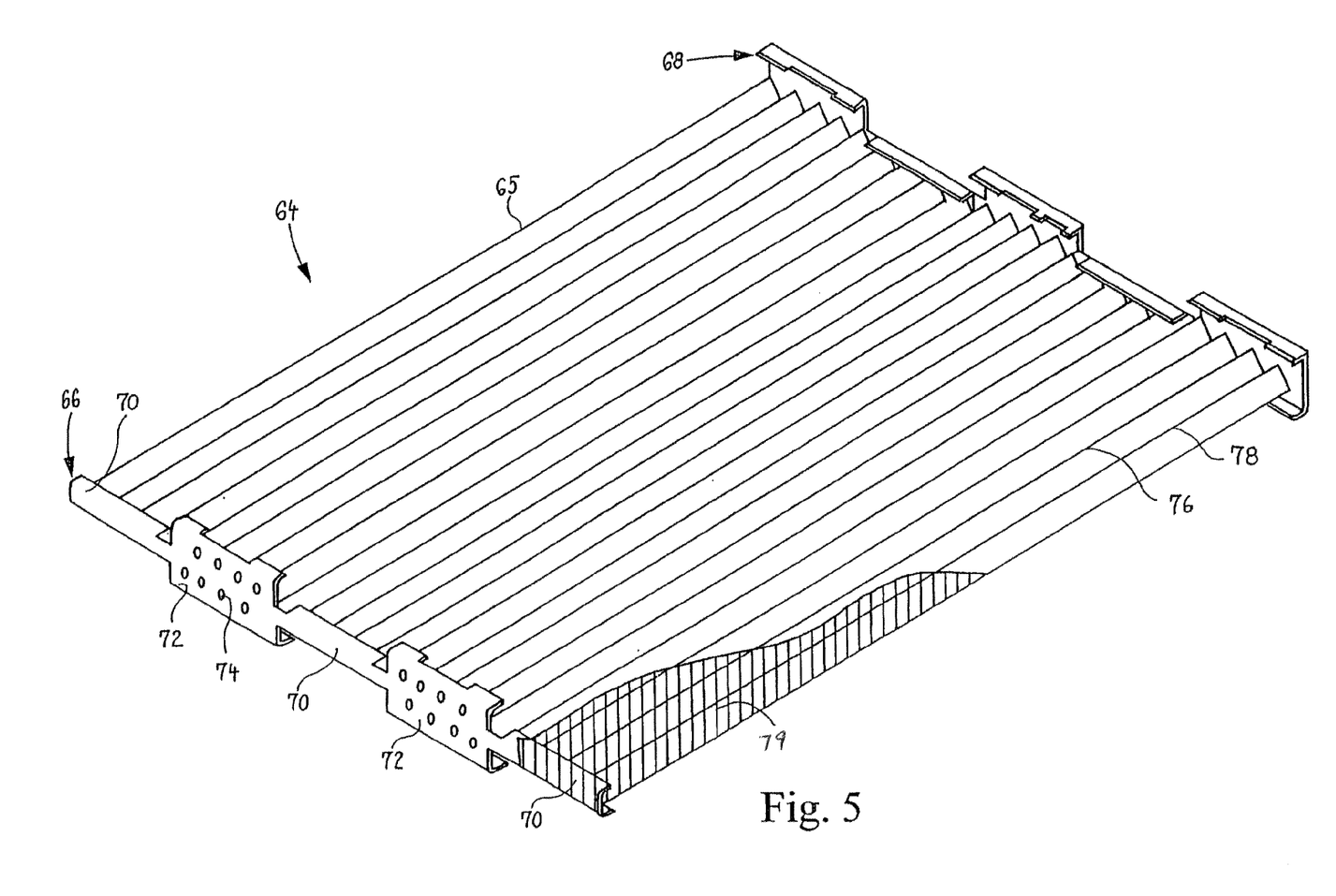
FIG. 5 is a schematic illustration of another tray according to the present invention.

FIG. 5 schematically illustrates a tray 64 in a perspective view. The tray 64 comprises twenty-two ridges, two neighbouring ridges being denoted 76 and 78. At each of the ends of the central body 65, wherein the ridges are defined, an end plate 66, 68 is positioned. The ridges extend parallel from one end of the central body to the other, however, embodiments where the ridges extend only part of the distance between the ends are also considered part of the present invention.

The end plate 66, and correspondingly the end plate 68, comprise sections where different widths are defined. The sections 70 define a width smaller than that defined at the sections 72. This is contemplated to improve the stacking of trays, i.e. to improve, or reduce, the chance/risk of trays sliding or shifting in relation to the other trays in a stack.

The position or location of the small and larger sections may be selected, as illustrated in the embodiment shown in FIG. 5. The one end plate may have a small or narrow section placed opposite a large or thick section at the opposite end of the tray 64.

The tray 64 illustrated in FIG. 5 includes a number of indentations or grooves 74 which may be used for an improved grip of a device gripping, lifting and/or moving the tray 64.

Figure 6:
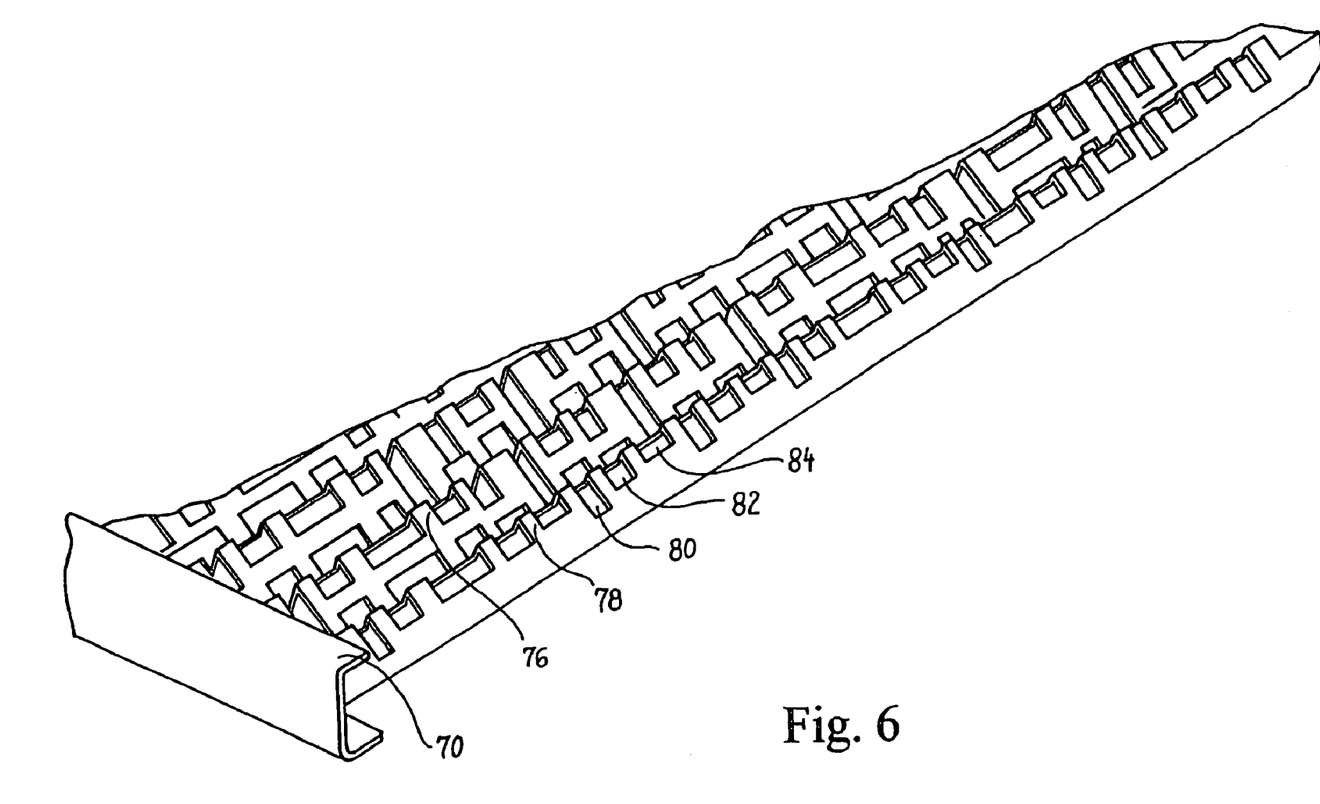
FIG. 6 is a schematic illustration of a detail of the tray of FIG. 5.

FIG. 6 schematically illustrates the hatched area 79 of FIG. 5. A number of apertures or openings are defined in the ridges.

A long or large aperture 80 is defined at one ridge. The aperture 80 has a mainly rectangular cross-section when viewed from above, which is also the case for the apertures 82 and 84.

The apertures 80, 82 and 84, serve several purposes. In one embodiment, or use, of the tray, two apertures in neighbouring ridges receive a flange of a syringe. The apertures are contemplated to improve the fixation of the syringe in the groove defined by the two neighbouring ridges. Also, the apertures or openings allow the syringe to be positioned in the groove with the body of the syringe being in facial contact in its entire length or at least a substantial part thereof.

When the tray with one or more syringes is disinfected, e.g. by applying hot steam or the like, such as when being in an autoclave, the steam or gas, may travel through the apertures to disinfect the outer surface of the syringes in the tray.

The steam or gas may travel through any of the apertures, including those where the flange of the syringe is received.

In alternative embodiments, the tray may include only apertures for receiving flanges of syringes. Further alternatively, the tray may include one set of apertures for receiving the flange of syringes and one or more additional sets of apertures.

The invention claimed is:

1. A tray for receiving a plurality of pre-filled syringes each having a tubular body defining an outer surface and a chamber having an open first end sealed with a plug and an open opposite second end configured to establish fluid communication with a hypodermic needle, wherein a flange extends from the tubular body at the first end, said tray comprising:
a plate defining a plurality of ridges alternating with a plurality of grooves parallel to said ridges, said ridges being interconnected with said grooves; and
a multitude of apertures in each of said ridges and extending through said plate, wherein each of the apertures is configured for (a) receiving a portion of the flange of one of the syringes when received in one of said grooves between two adjacent ridges of said plurality of ridges, and (b) permitting the passage of a gas through the plate to contact the outer surface of the syringe when received in the groove.

2. The tray according to claim 1, wherein said multitude of apertures in each ridge is distributed along a length of the ridge that exceeds a length defined between the first end and the second end of the syringe when received in the groove.

3. The tray according to claim 1, wherein each of the individual apertures in said multitude of apertures is rectangular.

4. The tray according to claim 1, wherein the ridges in said plurality of ridges are substantially parallel to each other.

5. The tray according to claim 1, wherein said tray defines a rectangular outer geometry having a pair of opposed short sides and a pair of opposed long sides, and wherein said tray further comprises an end plate at each of the opposed short sides of said tray.

6. The tray according to claim 5, wherein each of said end pieces comprises a first section defining a first width, and a second section defining a second width different from said first width.

7. The tray according to claim 5, wherein said plurality of ridges and said plurality of grooves are parallel to said long sides.

8. The tray according to claim 5, wherein said plurality of ridges and said plurality of grooves are parallel to said short sides.

9. The tray according to claim 1, wherein said multitude of apertures includes a first group of apertures that defines a first geometry and at least one additional group of apertures that defines at least one additional geometry different from said first geometry.

10. The tray according to claim 9, wherein said first geometry is a substantially rectangular geometry defining a first width and a second width, and wherein said at least one additional geometry is a substantially rectangular geometry defining a third width and a fourth width, said first width being smaller than said third width, and said second width being smaller than said fourth width, respectively.

11. The tray according to claim 9, wherein said first geometry is a substantially rectangular geometry defining a first width and a second width, and wherein said at least one additional geometry is a substantially rectangular geometry defining a third width and a fourth width, said first width being smaller than said third width, and said second width being smaller than said third width, respectively.

12. The tray according to claim 9, wherein said first geometry is a substantially rectangular geometry defining a first width and a second width, and wherein said at least one additional geometry is a substantially rectangular geometry defining a third width and a fourth width, said first width being smaller than said third width and said fourth width, and said second width being smaller than said fourth width and said third width, respectively.

13. The tray according to claim 9, wherein said first geometry is a square.

14. The tray according to claim 9, wherein each of the apertures in said first group of apertures is located between the apertures in said at least one additional group of apertures.

15. The tray according to claim 1, wherein said tray comprises a rigid material.

16. The tray according to claim 1, wherein each of said grooves is V-shaped.

\* \* \* \* \*

UNITED STATES PATENT AND TRADEMARK OFFICE
CERTIFICATE OF CORRECTION

| | | |
|---|---|---|
| PATENT NO. | : 8,011,506 B2 | Page 1 of 1 |
| APPLICATION NO. | : 11/721327 | |
| DATED | : September 6, 2011 | |
| INVENTOR(S) | : Flemming Hesseldahl | |

It is certified that error appears in the above-identified patent and that said Letters Patent is hereby corrected as shown below:

In column 1, line 25, after "a" delete "further on to a".

In column 2, line 66, delete "may by" and insert -- may be --, therefor.

Signed and Sealed this
Thirty-first Day of January, 2012

David J. Kappos
*Director of the United States Patent and Trademark Office*